| United States Patent [19] | [11] Patent Number: 4,735,941 |
|---|---|
| Freidinger et al. | [45] Date of Patent: Apr. 5, 1988 |

[54] 1,4-BENZODIAZEPINES WITH 5- AND 6-MEMBERED HETEROCYCLIC RINGS, USEFUL AS GASTROINTESTINAL AND CNS AGENTS

[75] Inventors: Roger M. Freidinger; Mark G. Bock, both of Hatfield; Ben E. Evans, Lansdale, all of Pa.

[73] Assignee: Merck & Co., Inc., Rahway, N.J.

[21] Appl. No.: 946,392

[22] Filed: Dec. 23, 1986

[51] Int. Cl.$^4$ .................... A61K 31/55; C07D 487/04
[52] U.S. Cl. .................................. 514/220; 540/559
[58] Field of Search ................ 540/559; 544/184; 514/220

[56] References Cited

U.S. PATENT DOCUMENTS

| 4,017,492 | 4/1977 | Moffet | 540/558 |
|---|---|---|---|
| 4,530,790 | 7/1985 | Monaghan et al. | 540/563 |
| 4,554,272 | 11/1985 | Bock et al. | 540/563 |
| 4,559,338 | 12/1985 | Bock et al. | 514/219 |
| 4,559,339 | 12/1985 | Bock et al. | 514/219 |
| 4,563,451 | 1/1986 | Bock et al. | 514/219 |
| 4,663,321 | 5/1987 | Rock et al. | 540/563 |
| 4,684,645 | 8/1987 | Chang et al. | 546/157 |

OTHER PUBLICATIONS

Kubota et al., Euro. J. Pharm., 110 (1985) 225–231.

Maten et al. Horm. Metabol. Res. 18 (1986) 2–9.
Jensen et al. Biochimica et Biophysica Acta, 757 (1983) 250–258.
Gardner et al. Derivative of CCK-(26–32) as Cholecystokinin Recepter Antagonists in Guinea Pig Pancreatic Acini, pp. 292–295.
Jensen et al., Proglumide Analogues: Patent Cholecystokinin Recepter Antagonists, pp. G214–G220.
Makovec et al., New Glutamic Acid Dervatives with Patent Competitive and Specific Cholecystokinin Activity, pp. 1048–1051.
Makovec et al., New Glutamic and Aspartic Derviatives Eur. J. Med. Chem.-Chim. Ther., 1986–21, No. 1, pp. 9–20.

*Primary Examiner*—Henry R. Jiles
*Assistant Examiner*—J. Richter
*Attorney, Agent, or Firm*—R. D. Meredith; R. A. Elder; Hesna J. Pfeiffer

[57] ABSTRACT

Aromatic 1,4-benxodiazepines with fused 5- or 6-membered heterocyclic rings which are antagonists of cholecystokinins and/or gastrin, and are useful in the treatment or prevention of CCK-related and/or gastrin-related disorders of the gastrointestinal, central nervous and appetite regulatory systems; compositions comprising these compounds; and methods of treatment employing these compounds.

15 Claims, No Drawings

1,4-BENZODIAZEPINES WITH 5- AND 6-MEMBERED HETEROCYCLIC RINGS, USEFUL AS GASTROINTESTINAL AND CNS AGENTS

BACKGROUND OF THE INVENTION

Cholecystokinins (CCK) and gastrin are structurally-related neuropeptides which exist in gastrointestinal tissue and in the the central nervous system (see, V. Mutt, *Gastrointestinal Hormones*, G. B. J. Glass, Ed., Raven Press, N.Y., p. 169 and G. Nisson, ibid, p. 127).

Cholecystokinins include CCK-33, a neuropeptide of thirty-three amino acids in its originally isolated form (see, Mutt and Jorpes, *Biochem. J.* 125, 678 (1971)), its carboxylterminal octapeptide, CCK-8 (a naturally-ocurring neuropeptide, also, and the minimum fully active sequence), and 39- and 12-amino acid forms, while gastrin occurs in 34-, 17- and 14-amino acid forms, with the minimum active sequence being the C-terminal pentapeptide, Gly-Trp-Met-Asp-Phe-$NH_2$, which is the common structural element shared by both CCK and gastrin.

CCK's are believed to be physiological satiety hormones, thereby possibly playing an important role in appetite regulation (G. P. Smith, *Eating and Its Disorders*, A. J. Stunkard and E. Stellar, Eds, Raven Press, New York, 1984, p. 67), as well as also stimulating colonic motility, gall bladder contraction, pancreatic enzyme secretion, and inhibiting gastric emptying. They reportedly co-exist with dopamine in certain mid-brain neurons and thus may also play a role in the functioning of dopaminergic systems in the brain, in addition to serving as neurotransmitters in their own right (see: A. J. Prange et al., "Peptides in the Central Nervous System", *Ann. Repts. Med. Chem.* 17, 31, 33 [1982] and references cited therein; J. A. Williams, *Biomed. Res.* 3 107 [1982]); and J. E. Morley, *Life Sci.* 30, 479, [1982]).

The primary role of gastrin, on the other hand, appears to be stimulation of the secretion of water and electrolytes from the stomach, and, as such, it is involved in control of gastric acid and pepsin secretion. Other physiological effects of gastrin then include increased mucosal blood flow and increased antral motility, with rat studies having shown that gastrin has a positive trophic effect on the gastric mucosa, as evidenced by increased DNA, RNA and protein synthesis.

Antagonists to CCK and to gastrin have been useful for preventing and treating CCK-related and/or gastrin-related disorders of the gastrointestinal (GI) and central nervous (CNS) systems of animals, especially of humans. Just as there is some overlap in the biological activities of CCK and gastrin, antagonists also tend to have affinity for both receptors. In a practical sense, however, there is enough selectivity to the different receptors that greater activity against specific CCK- or gastrin-related disorders can often also be identified.

Selective CCK antagonists are themselves useful in treating CCK-related disorders of the appetite regulatory systems of animals as well as in potentiating and prolonging opiate-mediated analgesia, thus having utility in the treatment of pain [see P. L. Faris et al., Science 226, 1215 (1984)], while selective gastrin antagonists are useful in the modulation of CNS behavior, as a palliative for gastrointestinal neoplasms, and in the treatment and prevention of gastrin-related disorders of the gastrointestinal system in humans and animals, such as peptic ulcers, Zollinger-Ellison syndrome, antral G cell hyperplasia and other conditions in which reduced gastrin activity is of therapeutic value.

Also, since CCK and gastrin also have trophic effects on certain tumors [K. Okyama, *Hokkaido J. Med Sci.*, 60, 206–216 (1985)], antagonists of CCK and gastrin are useful in treating these tumors [see, R. D. Beauchamp et al., *Ann. Surg.*, 202,303 (1985)].

Four distinct chemical classes of CCK-receptor antagonists have been reported. The first class comprises derivatives of cyclic nucleotides, of which dibutyryl cyclic GMP has been shown to be the most potent by detailed structure-function studies (see, N. Barlos et al., *Am. J. Physiol.*, 242, G 161 (1982) and P. Robberecht et al., *Mol., Pharmacol.*, 17, 268 (1980)).

The second class comprises peptide antagonists which are C-terminal fragments and analogs of CCK, of which both shorter (Boc-Met-Asp-Phe-$NH_2$, Met-Asp-Phe-$NH_2$), and longer (Cbz-Tyr($SO_3H$)-Met-Gly-Trp-Met-Asp-$NH_2$) C-terminal fragments of CCK can function as CCK antagonists, according to recent structure-function studies (see, R. T. Jensen et al., *Biochem. Biophys. Acta.*, 757, 250 (1983), and M. Spanarkel et al., *J. Biol. Chem.*, 258, 6746 (1983)). The latter compound was recently reported to be a partial agonist [see, 8. M. Howard et al., *Gastroenterology* 86(5) Part 2, 1118 (1984)].

Then, the third class of CCK-receptor antagonists comprises the amino acid derivatives: proglumide, a derivative of glutaramic acid, and the N-acyl tryptophans. including para-chlorobenzoyl-L-tryptophan (benzotript), [see, W. F. Hahne et al., *Proc. Natl. Acad. Sci. U.S.A.*, 78, 6304 (1981), R. T. Jensen et al., *Biochem. Biophys. Acta.*, 761, 269 (1983)]. All of these compounds, however, are relatively weak antagonists of CCK ($IC_{50}$: generally $10^{-4}M$[although more potent analogs of proglumide have been recently reported in F. Makovec et al., *Arzneim-Forsch Drug Res.*, 35 (II), 1048 (1985) and in German Patent Application DE 3522506A1], but down to $10^{-6}M$ in the case of peptides), and the peptide CCK-antagonists have substantial stability and absorption problems.

In addition, a fourth class consists of improved CCK-antagonists comprising a nonpeptide of novel structure from fermentation sources [R. S. L. Chang et al., *Science*, 230, 177–179 (1985)] and 3-substituted benzodiazepines based on this structure [published European Patent Applications Nos. 167 919, 167 920 and 169 392, B. E. Evans et al, *Proc. Natl. Acad. Sci. U.S.A.*, 83, p. 4918–4922 (1986) and R. S. L. Chang et al, ibid, p. 4923–4926] have also been reported.

No really effective receptor antagonists of the in vivo effects of gastrin have been reported (J. S. Morley, *Gut Pept. Ulcer Proc.*, Hiroshima Symp. 2nd, 1983, p. 1), and very weak in vitro antagonists, such as proglumide and certain peptides have been described [(J. Martinez, *J. Med. Chem.* 27, 1597 (1984)]. Recently, however, pseudopeptide analogs of tetragastrin have been reported to be more effective gastrin antagonists than previous agents [J. Martinez et al., *J. Med. Chem.*, 28, 1874–1879 (1985)].

The benzodiazepine (BZD) structure class, which has been widely exploited as therapeutic agents, especially as central nervous system (CNS) drugs, such as anxiolytics, and which exhibits strong binding to "benzodiazepine receptors" in vitro, has not in the past been reported to bind to CCK or gastrin receptors. Benzodiazepines have been shown to antagonize CCK-induced activation of rat hippocampal neurones but this effect is mediated by the benzodiazepine receptor, not the CCK receptor [see J. Bradwejn et al., Nature, 312, 363 (1984)]. Of these reported BZD's, additionally, the large majority do not contain substituents attached to the 3-position of the seven membered ring, as it is well known in the art that 3-substituents result in decreasing anxiolitic activity, especially as these substituents increase in size. Further, it has been demonstrated that in the case of the 3-substituted benzodiazepines that have been reported, the preferred stereochemistry at position 3 for CNS activity is S, which would correspond to an L-amino acid, such as L-tryptophan.

It was, therefore, an object of this invention to identify substances which more effectively antagonize the function of cholecystokinins and/or gastrin in disease states in mammals, especially in humans. It was another object of this invention to prepare novel compounds which more selectively inhibit cholecystokinins or inhibit gastrin. It was still another object of this invention to develop a method of antagonizing the functions of cholecystokinin and/or gastrin in disease states in mammals. It is also an object of this invention to develop a method of preventing or treating disorders of the gastrointestinal, central nervous and appetite regulatory systems of mammals, especially of humans, or of increasing food intake of animals.

SUMMARY OF THE INVENTION

The present invention is directed to aromatic 1,4-benzodiazepines with fused 5- and 6-membered heterocyclic rings which are antagonists of cholecystokinins (CCK) and/or gastrin, and are useful in the treatment and prevention of CCK-related and/or gastrin-related disorders of the gastrointestinal, central nervous and appetite regulatory systems of mammals, especially of humans, including irritable bowel syndrome, ulcers, excess pancreatic or gastric secretion, acute pancreatitis, motility disorders, neuroleptic disorders, tardive dyskinesia, Parkinson's disease, psychosis, Gilles de la Tourette Syndrome, disorders of the appetite regulatory system, Zollinger-Ellison syndrome, antral G cell hyperplasia, pain (by the potentiation of opioid analgesics), and malignancies of the lower esophagus, stomach, intestines, and colon. As antagonists of CCK, they may also be used to increase food intake in animals.

DETAILED DESCRIPTION OF THE INVENTION

The 1,4-benzodiazepines with fused 5- and 6-membered heterocyclic rings of this invention are those of Formula I:

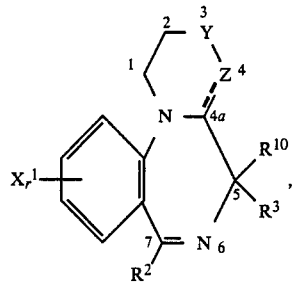

wherein
$R^1$ is H or $C_1$–$C_4$-straight- or branched-chain alkyl;
$R^2$ is H, $C_1$–$C_4$-straight- or branched-chain alkyl, mono- or disubstituted or unsubstituted phenyl (where the substituent(s) is/are independently selected from the group consisting of halo, $C_1$–$C_4$-alkyl, $C_1$–$C_4$-alkoxy, $C_1$–$C_4$-alkylthio, carboxyl, carboxyl-$C_1$–$C_4$-alkyl, nitro, —$CF_3$,

and hydroxy), 2-, 3- or 4-pyridyl, or —$(CH_2)_m COOR^6$;
$R^3$ is

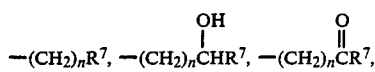

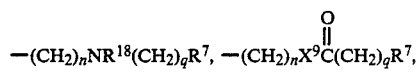

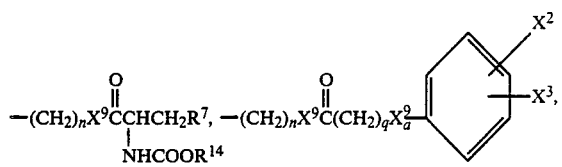

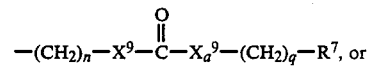

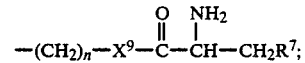

$R^4$ and $R^5$ are independently H, $C_1$–$C_4$-straight- or branched-chain-alkyl, cyclo-$C_3$–$C_7$-alkyl, or are connected to form a hetero ring of the form,

where k is 2 to 6;
$R^6$ is H, $C_1$–$C_4$-straight or branched-chain alkyl, cyclo-$C_3$–$C_7$-alkyl, unsubsitituted or mono- or disubstituted phenyl (where the substituent(s) is/are independently selected from the group consisting of halo, $C_1$–$C_4$-alkyl, $C_1$–$C_4$-alkoxy, nitro, and $CF_3$), or unsubstituted or mono- or disubstituted phenyl-$C_1$–$C_4$-straight or branched-chain alkyl (where the substituent(s) is/are independently selected from the group consisting of halo, $C_1$–$C_4$-alkyl, $C_1$–$C_4$-alkoxy, nitro, and $CF_3$);
$R^7$ is α- or β-naphthyl, unsubstituted or mono- or disubstituted phenyl (where the substituent(s) is/are independently selected from the group consisting of halo, —$NO_2$, —OH, —$NR^4R^5$, $C_1$–$C_4$-straight- or branched-chain alkyl, cyano, phenyl, trifluoromethyl, acetylamino, acetyloxy, $C_1$–$C_4$-straight- or branched-chain alkylthio, $SCF_3$, C≡CH, $CH_2SCF_3$, $OCHF_2$, S-phenyl, or $C_1$–$C_4$-straight- or branched-chain alkoxy),

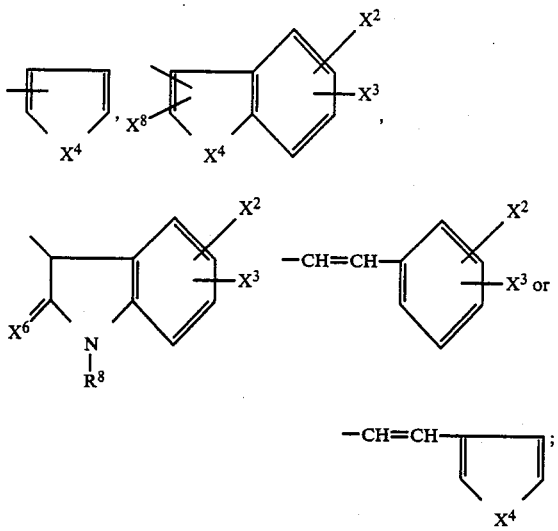

$R^8$ is H, $C_1$–$C_4$-straight- or branched-chain alkyl, cyclo-$C_3$–$C_7$-alkyl, —$(CH_2)_n$— cyclo-$C_3$–$C_7$-alkyl,

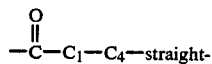

or branched-chain alkyl, or

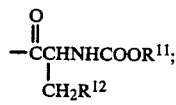

$R^{10}$ is H, —OH, or —$CH_3$;
$R^{11}$ and $R^{12}$ are independently $C_1$–$C_4$-straight- or branched-chain alkyl or cyclo-$C_3$–$C_7$-alkyl;
$R^{14}$ is $C_1$–$C_4$-straight- or branched-chain alkyl or phenyl-$C_1$–$C_4$-straight- or branched-chain alkyl;
$R^{18}$ is H, $C_1$–$C_4$-straight- or branched-chain alkyl or formyl, acetyl, propionyl or butyryl;
m is 1-to-4;
n is 0-to-4;
q is 0-to-4;
r is 1 or 2;
$X^1$ is H, —$NO_2$, $CF_3$, CN, OH, $C_1$–$C_4$-straight- or branched-chain alkyl, halo, $C_1$–$C_4$-straight- or branched-chain alkylthio, $C_1$–$C_4$-straight- or branched-chain alkoxy, —$(CH_2)_nCOOR^6$, —$NR^4R^5$, or

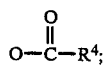

$X^2$ and $X^3$ are independently H, —OH, —$NO_2$, halo, $C_1$–$C_4$-straight- or branched-chain alkylthio, $C_1$–$C_4$-straight- or branched-chain alkyl, $C_1$–$C_4$-straight- or branched-chain alkoxy, or

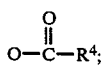

$X^4$ is S, O, $CH_2$, or $NR^8$;

$X^6$ is O or HH;
$X^8$ is H or $C_1$–$C_4$-straight- or branched-chain alkyl;
$X^9$ and $X_a^9$ are independently $NR^{18}$ or O;
Y=$CH_2$, $NR^1$, or is absent; and
Z=N or $CH_2$,
and the pharmaceutically-acceptable salts thereof.

As used herein, the definition of each expression, i.e., m, n, p, $C_1$–$C_4$-alkyl, etc., when it occurs more than once in any structure, is intended to be independent of its definition elsewhere in the same structure.

In the compounds of Formula I, the preferred stereochemistry for CCK-antagonism relates to D-tryptophan, where $C^{4a}$ and $N^6$ of Formula I ($C^{3a}$ and $N^5$ for 5-membered heterocycles) correspond to the carbonyl carbon and α-amino nitrogen, respectively, of D-tryptophan and $R^3$ occupies the position of the indolylmethyl side chain.

In the compounds of Formula I, the preferred stereochemistry for gastrin antagonism may be either D or L depending on the nature of $R^3$. For example, when $R^3$=$(CH_2)_nR^7$ or

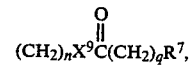

the preferred stereochemistry corresponds to D-tryptophan, as above. When

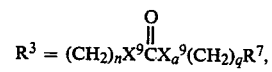

the preferred stereochemistry corrsponds to L-tryptophan.

As used herein, halo is F, Cl, Br, or I; and $C_1$–$C_4$-alkyl includes methyl, ethyl, propyl, isopropyl, butyl, isobutyl, and t-butyl.

Preferred compounds according to the present invention include those wherein $R^1$ is H or methyl; $R^2$ is phenyl or o-F-phenyl; $R^3$ is

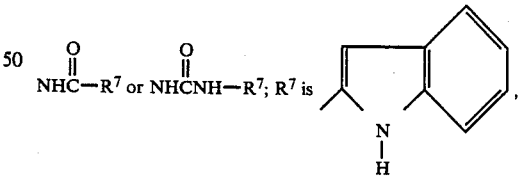

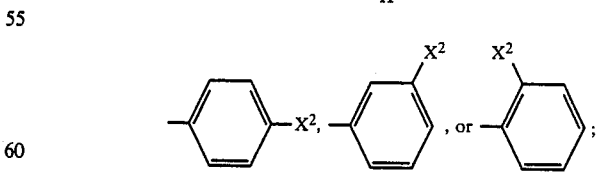

$X^1$ is H; $X^2$ is H, —$NO_2$, halo, methyl or methoxy; Y is absent and Z is $CH_2$; or Y is absent and Z is N; or Y is $NR^1$ and Z is $CH_2$; or Y is $CH_2$ and Z is $CH_2$; or Y is $CH_2$ and Z is N. For preventing gastrin-related problems preferred compounds include those wherein $R^3$ is

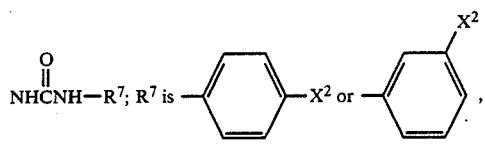

and the stereochemistry corresponds to L-tryptophan. For preventing and treating CCK-related problems preferred compounds include those wherein $R^3$ is

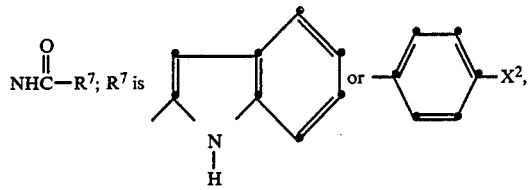

where $X^2$ is halo, and wherein $R^3$ is

where $R^7$ is

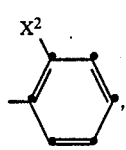

and the sterochemistry corresponds to D-tryptophan.

Even more particularly preferred compounds include, for CCK antagonism:
4(S)-4(2-indolecarbonylamino)-6-phenyl-2,3,3a,4-tetrahydro-1H-pyrrolo[1,2-a]-[1,4]-benzodiazepine;
5(S)-5(4-chlorophenylcarbonylamino)-7-phenyl-1,2,3,4,4a,5-hexahydropyrido-[1,2-a]-[1,4]-benzodiazepine;
5(S)-5-(2-indolecarbonylamino)-3-methyl-7-phenyl-1,2,3,4,4a,5-hexahydro-pyrazino[1,2a]-[1,4]-benzodiazepine;
4(S)2,4-dihydro-4-(2-indolecarbonylamino)-6-phenyl-1H-imidazo[1,2-a]-[1,4]-benzodiazepine; or
5(S)-5-(2-indolecarbonylamino)-7-phenyl-1,2,3,5-tetrahydropyrido[1,2-a]-[1,4]-benzodiazepine;
or for gastrin antagonism:
4(R)-4(3-methoxyphenylaminocarbonylamino)-6-phenyl-2,3,3a,4-tetrahydro-1H-pyrrolo[1,2-a]-[1,4]-benzodiazepine;
5(R)-5-(3-methylphenylaminocarbonylamino)-7-phenyl-1,2,3,4,4a,5-hexahydropyrido-[1,2,-a]-[1,4]-benzodiazepine;
5(R)-5-(3-chlorophenylaminocarbonylamino)-3-methyl-7-phenyl-1,2,3,4,4a,5-hexahydroprazino-[1,2-a]-[1,4]-benzodiazepine;
4(R)-2,4-dihydro-4-(3-methoxyphenylaminocarbonylamino)-6-phenyl-1H-imidazo-[1,2-a]-[1,4]-benzodiazepine; or
5(R)-5-(3-methylphenylaminocarbonylamino)-7-phenyl-1,2,3,5-tetrahydropyrido-[1,2-a]-[1,4]-benzodiazepine.

The pharmaceutically-acceptable salts of the compounds of Formula I include the conventional non-toxic salts or the quaternary ammonium salts of the compounds of Formula I formed, e.g., from non-toxic inorganic or organic acids. For example, such conventional non-toxic salts include those derived from inorganic acids such as hydrochloric, hydrobromic, sulfuric, phosphoric, nitric and the like; and the salts prepared from organic acids such as acetic, propionic, succinic, glycolic, stearic, lactic, malic, tartaric, citric, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, isethionic, and the like.

The compounds of Formula I are particularly distinguished from benzodiazepines of the prior art by the presence of 3-substituents. These Formula I compounds bind strongly to CCK-receptors, but only weakly to benzodiazepine-receptors, especially with the increasing size of the 3-substituent.

Compounds according to Formula I may be prepared according to Schemes I through VI as follows:

REACTION SCHEME I

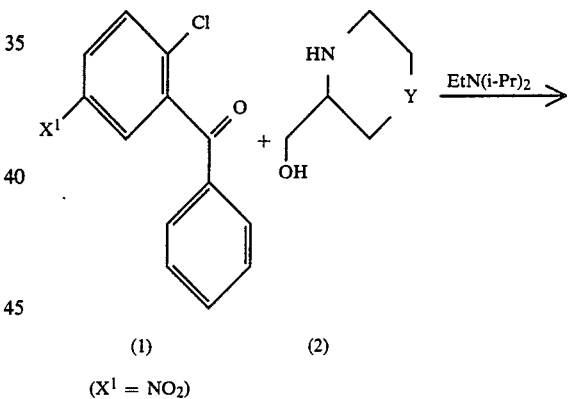

($X^1 = NO_2$)

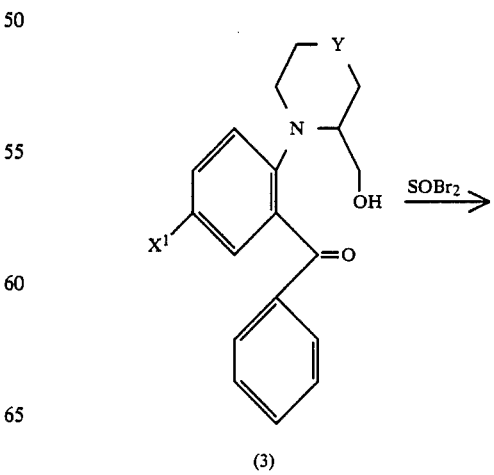

9
-continued
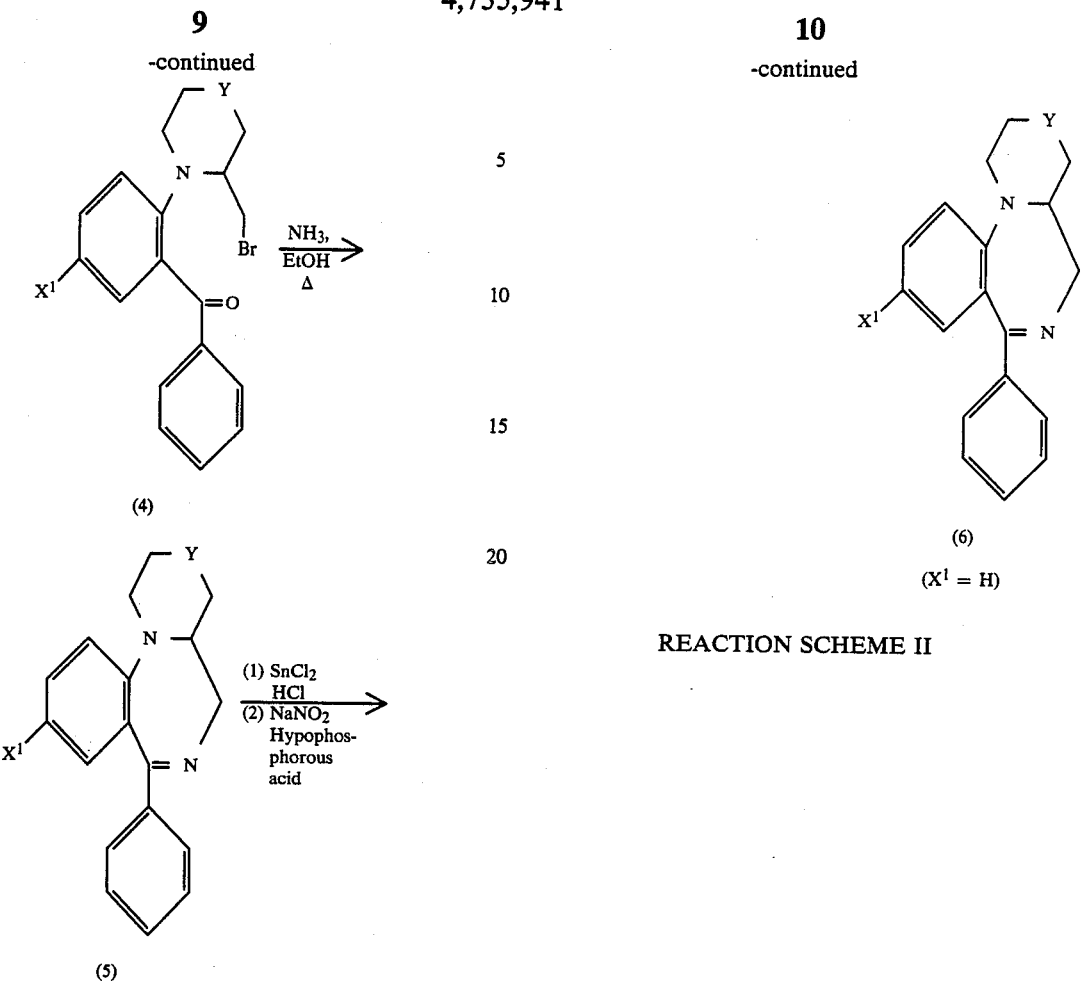
(4)
(5)
10
-continued
(6)
($X^1$ = H)
REACTION SCHEME II
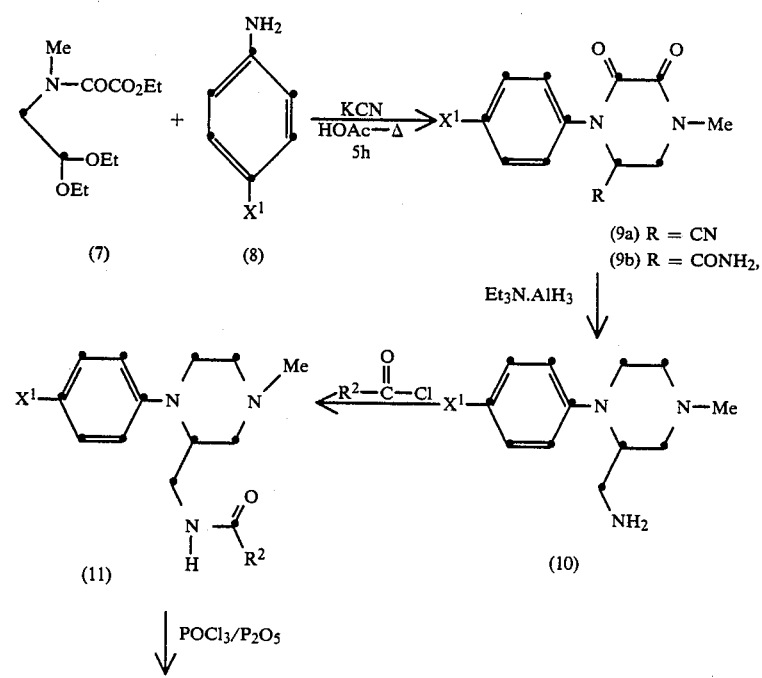
(7) (8) (9a) R = CN
(9b) R = $CONH_2$,
(11) (10)

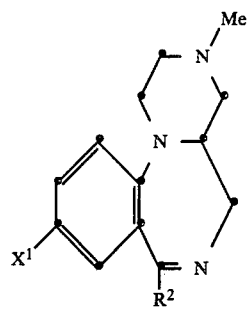
(12)
REACTION SCHEME III
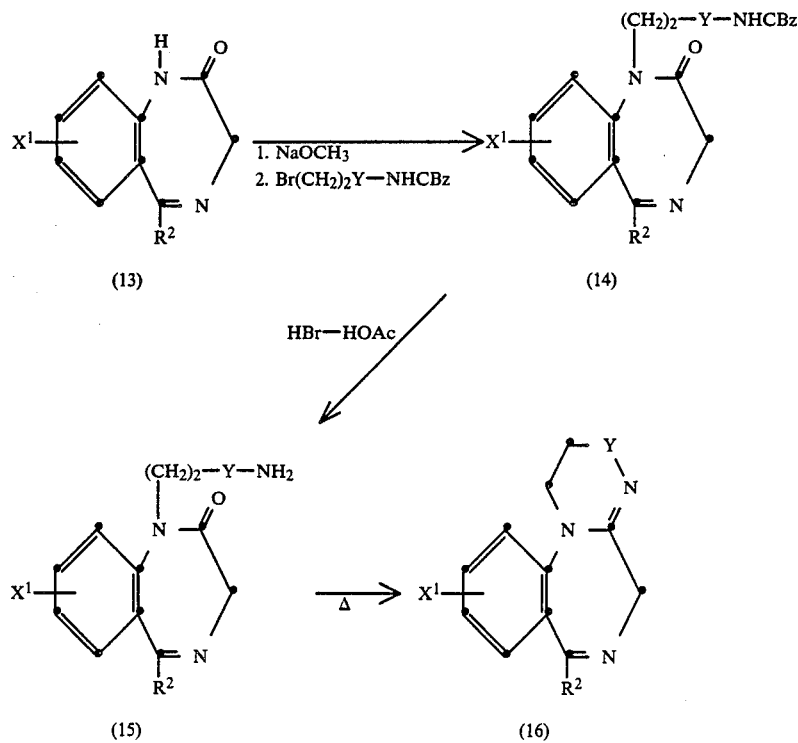
(Y = $CH_2$ or is absent)
REACTION SCHEME IV
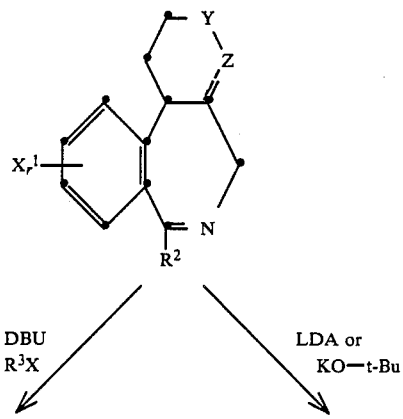

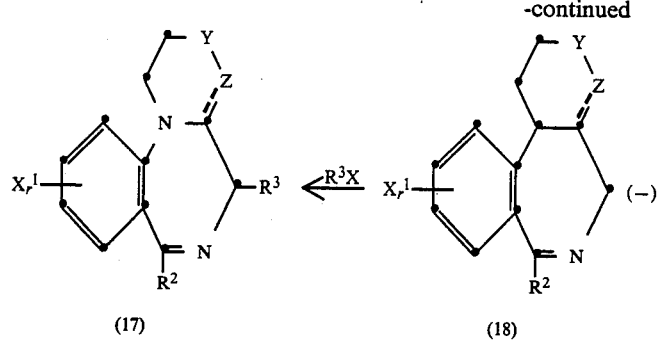
(where, in the definition of $R^3$, n is at least 1, when the attachment atom to $R^7$ is C; otherwise, n is at least 2)
REACTION SCHEME IV (CONT'D)
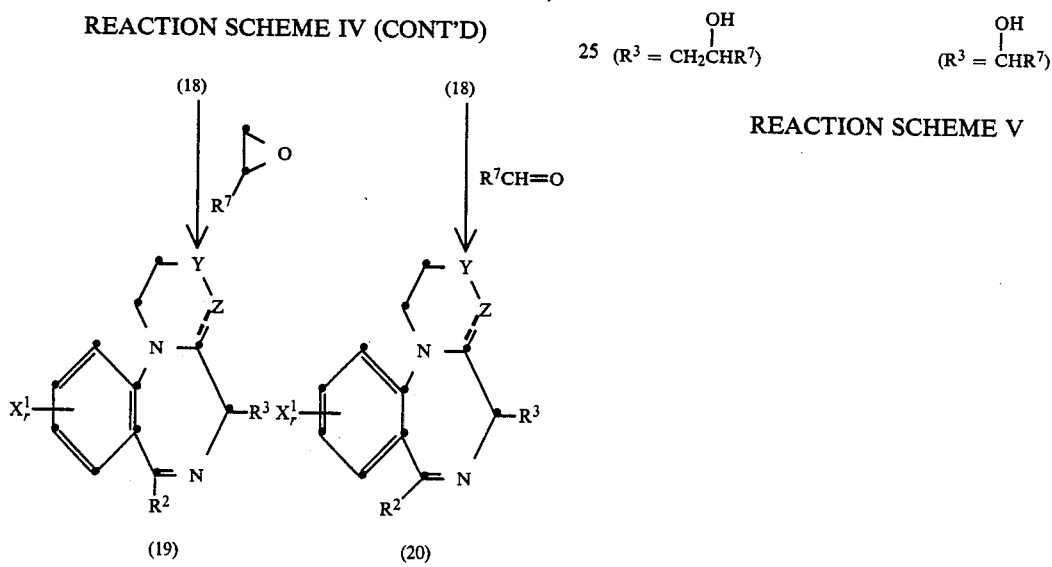
REACTION SCHEME V
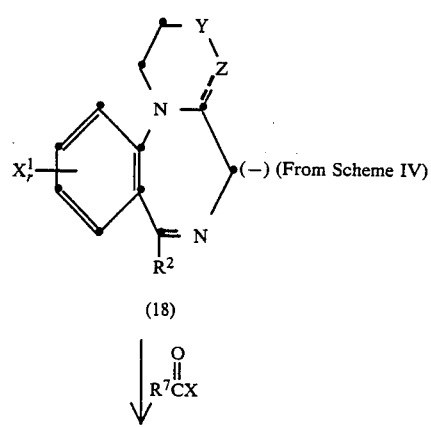

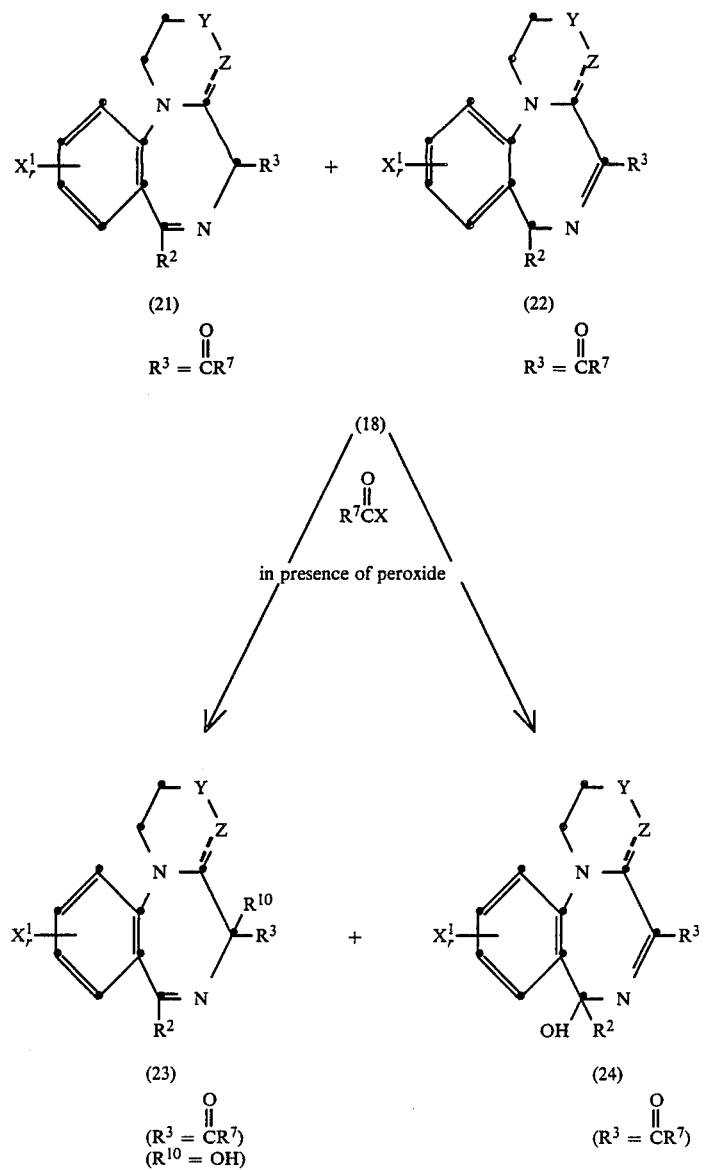
REACTION SCHEME VI
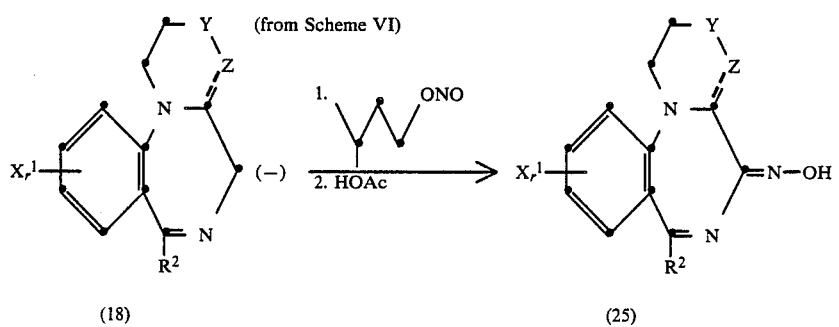

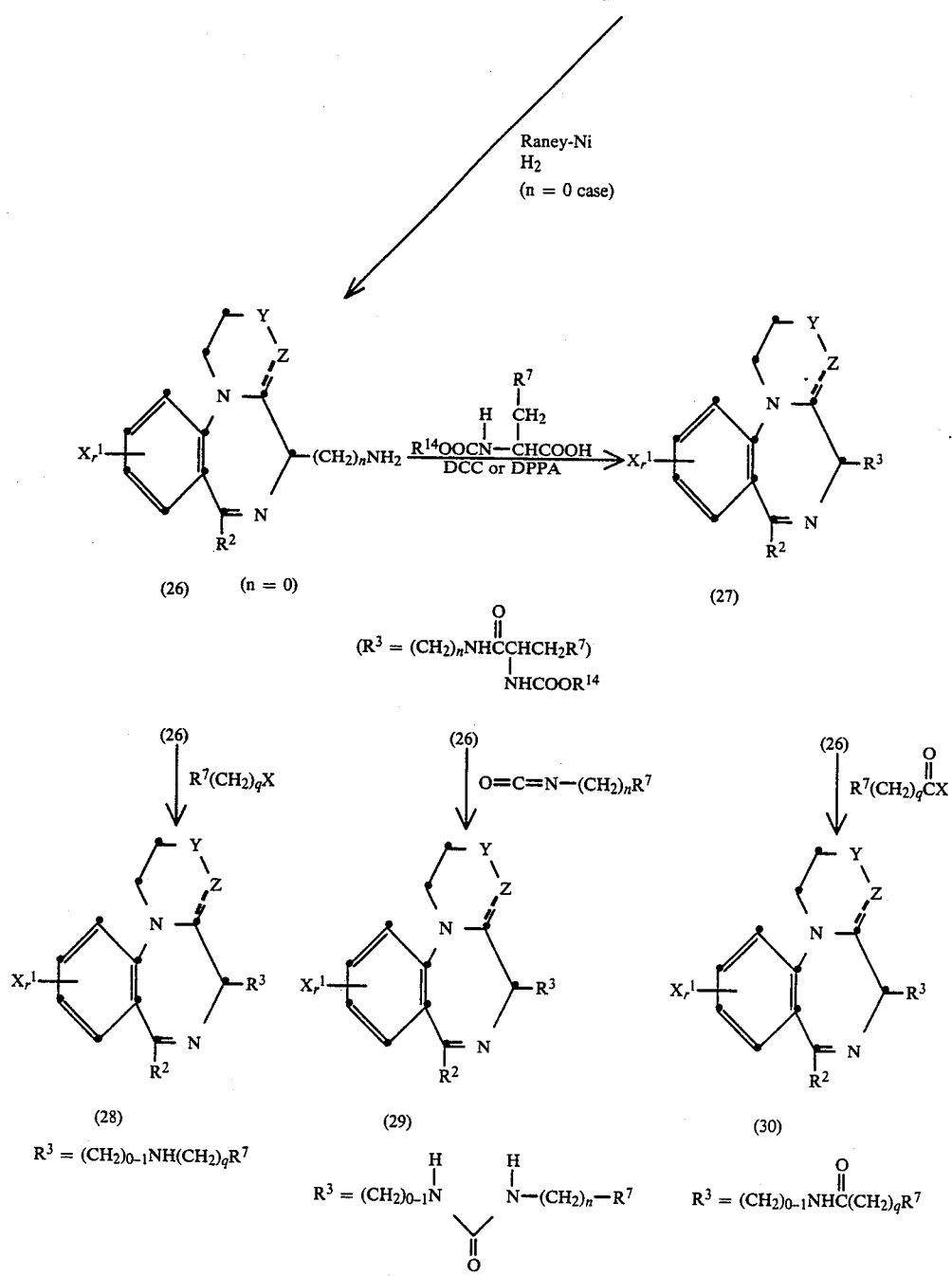

Referring to Reaction Scheme I, a mixture of benzophenone (1), alcohol (2), diisopropylethylamine, and N-methyl-2-pyrrolidine is heated for 10-20 hours to give alcohol (3). This alcohol is treated with thionyl bromide to provide bromide (4). Heating of (4) with ammonia in ethanol in an autoclave produces the benzodiazepine (5). The nitro group in (5) is selectively reduced with stannic chloride in HCl to an amine which is deaminated under Sandmeyer conditions yielding (6).

An alternative synthesis of hexahydropiperazinobenzodiazepines is shown in Reaction Scheme II. The 2, 3 piperazindiones (9) are obtained by heating ethyl N-(2,2-diethoxyethyl)-N-methyloxamate (7) with p-substituted aniline (8) and potassium cyanide in acetic acid. A small amount of the corresponding carboxamide derivative resulting from hydrolysis of the nitrile is often observed. Reaction of (9a) with alane-triethylamine complex yielded the primary amine (10). Acylation of (10) is accomplished by using the appropriate carboxylic acid chlorides to yield (11), which cyclize smoothly when heated with a mixture of phosphorus oxychloride and phosphorus pentoxide to yield the desired hexahydropyrazino[1,2-a][1,4,]benzodiazepines (12).

Referring now to Reaction Scheme III, benzodiazepine (13) is treated first with sodium methoxide and then with carbobenzoxybromoethyl- or propylamine to give (14). Compound (14) is then treated with a solution of HBr in glacial acetic acid to give the free amino derivative (15). The cyclodehydration product (16) is formed by heating (15) under reflux in ethanol.

Referring now to Reaction Scheme IV, the anion (18) is generated from compounds produced in Schemes I–V by the procedure of *J. Org. Chem.*, 46, 3945 (1981) using lithium diisopropylamide (LDA) or using potassium tert-butoxide.

(18) can be variously treated. For example, the hydroxy alkyl derivative (20) is generated by adding an aldehyde to a solution of (18). Treatment of (18) with an epoxide yields the hydroxyethyl derivative (19). By treating (18) with an alkyl halide, the alkyl derivative (17) is produced.

An alternative procedure for obtaining (17) is to treat the compounds from Scheme III with an alkyl halide and a strong base such as 1,8-diazabicyclo[5.4.0]undec-7-ene (DBU) and heating.

Reaction Scheme V describes the formation of $R^3$=keto compounds of Formula I. These are produced by treating the anion (18) with an acid halide or anhydride. This reaction usually produces both isomers (21) and (22). When the reaction is run in the presence of peroxide, the hydroxy compounds (23) and (24) are produced.

Reaction Scheme VI describes the formation of Formula I compounds where $R^3$ is a substituted amino moiety. The amino compounds (26) may be obtained by nitrosation of (18) followed by reduction of the oxime (25) with Raney nickel and hydrogen.

When (26) is treated with an alkyl halide, the N-alkyl derivative (28) is produced.

Treatment of (26) with an acid halide or anhydride produces the N-acyl derivative (30).

Compound (26) may also be treated with an N-protected α-amino acid and a coupling reagent such as DCC or DPPA (diphenylphosphorylazide) to give the amides of structure (27).

Treatment of compound (26) with an isocyanate gives the ureas (29).

The pharmaceutically-acceptable salts of the compounds of present invention may be synthesized from the compounds of Formula I which contain a basic moiety by conventional chemical methods. Generally, the salts are prepared by reacting the free base with stoichiometric amounts of or with an excess of the desired salt-forming inorganic or organic acid in a suitable solvent or in various combinations of solvents.

Screening of the novel compounds according to the present invention to determine biological activity and obtain an $IC_{50}$ value for them, in order to identify significant CCK-antagonism, may be accomplished using an $^{125}I$-CCK-receptor binding assay and in vitro isolated tissue preparations. In order to identify significant gastrin antagonism, $^{125}I$-gastrin and $^3H$-pentagastrin binding assays are used. These tests involve the following:

CCK Receptor Binding (Pancreas) Method

CCK-8, radiolabeled with $^{125}I$-Bolton Hunter reagent (2000 Ci/mmole) is purchased from New England Nuclear (NEN) and receptor binding is performed according to Innis and Snyder (*Proc. Natl. Acad. Sci.*, 77, 6917–6921, 1980), with minor modifications as described in Chang and Lotti (*Proc. Natl. Acad. Sci. USA*, 83, 4923–4926, 1986).

The whole pancreas of a male Sprague-Dawley rat (200–350 g), which has been sacrificed by decapitation, is dissected free of fat tissue and homogenized in 20 volumes of ice-cold 50 mm Tris HCl (pH 7.7 at 25° C.) with a Brinkmann Polytron PT-10. The homogenates are centrifuged at 48,000 g for 10 minutes, then the resulting pellets are resuspended in Tris Buffer, centrifuged as above, and resuspended in 200 volumes of binding assay buffer (50 mm Tris HCl, pH 7.7 at 25° C., 5 mm dithiothreitol and 0.1 mm bacitracin).

For the binding assay, 25 µl of buffer (for total binding), or unlabeled CCK-8 sulfate sufficient to give a final concentration of 1 µM of CCK-8 (for nonspecific binding), or the compounds according to the instant invention (for determination of antagonism to $^{125}I$-CCK binding) and 25 µl of $^{125}I$-CCK-8 (30,000–40,000 cpm), are added to 450 µl of the membrane suspensions in duplicate or triplicate test tubes. The reaction mixtures are incubated at 37° C. for 30 minutes and then filtered on glass fiber GF/B filters, which are then rapidly washed with 3×4 ml of ice cold Tris HCl containing 1 mg/ml BSA, and the filters are counted with a Beckman Gamma 5000. For Scatchard analysis to determine the mechanism of inhibition of $^{125}I$-CCK binding by the most potent compounds (*Ann. N.Y. Acad. Sci.*, 51, 660, 1949), $^{125}I$-CCK-8 is progressively diluted with increasing concentrations of CCK-8.

CCK Receptor Binding (Brain) Method $^{125}I$-CCK-8 binding is performed similarily to the method described by Saito et al. (*J. Neurochem.*, 37, 483–490, 1981), with modifications described by Chang and Lotti (*Proc. Natl. Acad. Sci. USA*, 83 4923–4926, 1986).

Male Hartley guinea pigs (300–500 g) are sacrificed by decapitation, and the brains are removed and placed in ice-cold 50 mm Tris HCl (Trizma-7.4) [pH 7.4 at 25° C.]. The cerebral cortex is dissected and used as a receptor source and each gram of fresh guinea pig brain tissue is homogenized in 10 ml of Tris/Trizma buffer with a Brinkmann polytron PT-10. The homogenates are centrifuged at 42,000 g for 15 minutes, then the resulting pellets are resuspended in 200 volumes of binding assay buffer (10 mM N-2-hydroxy-ethylpiperazine-N'-2-ethenesulfonic acid (HEPES), 5 mM $MgCl_2$, 1 mM ethyleneglycol-bis-(β-aminoethylether)-N,N-tetraacetic acid (EGTA), 0.4% BSA (bovine serum albumin) and 0.25 mg/ml bacitracin, pH 6.5).

The remainder of the binding assay method is as described for the pancreas method, except that the reaction mixtures are incubated at 25° C. for 2 hours before centrifugation.

Isolated Guinea Pig Gall Bladder Method

The two halves of the gall bladders, free of adjacent tissue, of male Hartley guinea pigs (400–600 g), which have been sacrificed by decapitation, are suspended under 1 g tension along the axis of the bile duct in 15 ml organ bath, containing a Kreb's bicarbonate solution of 118 mm NaCl, 4.75 mm KCl, 2.54 mm $CaCl_2$, 1.19 mm $KH_2PO_4$, 1.2 mm $MgSO_4$, 25 mm $NaHCO_3$ and 11 mm dextrose, which is maintained at 32° C. and bubbled with a mixture of 95% $O_2$ and 5% $CO_2$. The tissues are washed every 10 minutes for one hour to obtain equilibrium prior to the beginning of the study and the isometric contractions of the strips are recorded using Statham (60 g: 0.12 mm) strain gauges and a Hewlett-Packard 77588 recorder.

CCK-8 is added cumulatively to the baths and $EC_{50}$'s are determined using regression analysis. After washout (every 10 minutes for one hour), the compound to be tested is added at least 5 minutes before the addition of CCK-8 and the EC$_{50}$ of CCK-8 in the presence of compound to be tested is similarly determined.

A shift to the right of the CCK dose response curve without reduction of the maximal centractile response, indicates competitive antagonism of CCK from this method.

Isolated Longitudinal Muscle of Guinea Pig Ileum

Longitudinal muscle strips with attached nerve plexus are prepared as described in *Brit. J. Pharmac.* 23:; 356–363, 1964; *J. Physiol.* 194: 13—33, 1969. Male Hartley guinea pigs are decapitated and the ileum removed (10 cm of the terminal ileum is discarded and the adjacent 20 cm piece used), with a 10 cm piece of the ileum being stretched on a glass pipette. Using a cotton applicator to stroke tangentially away from the mesentery attachment at one end, the longitudinal muscle is separated from the underlying circular muscle and the longitudinal muscle is tied to a thread and by gently pulling, stripped away from the entire muscle. A piece of approximately 2 cm is suspended in 5 ml organ bath containing Krebs solution and bubbled with 95% $O_2$ and 5% $CO_2$ at 37° C. under 0.5 g tension. CCK-8 is added cumulatively to the baths and EC$_{50}$ values in the presence and absence of compounds to be tested are determined, as described in the gall bladder protocol above.

Gastrin Receptor Binding In Guinea Pig Gastric Glands

Guinea pig gastric mucosal glands are prepared by the procedure of Berglingh and Obrink, *Acta Physiol. Scand.* 96: 150 (1976), with a slight modification according to Praissman et al. *C. J. Receptor Res.* 3: (1983). Gastric mucosa from male Hartley guinea pigs (300–500 g body weight) are washed thoroughly and minced with fine scissors in standard buffer consisting of the following: 130 mm NaCl, 12 mm NaHCO$_3$, 3 mm NaH$_2$PO$_4$, 3 mm Na$_2$HPO$_4$, 3 mm K$_2$HPO$_4$, 2 mm MgSO$_4$, 1 mm CaCl$_2$, 5 mm glucose, 4 mm L-glutamine and 25 mm HERPES at pH 7.4. The minced tissues are washed and incubated in a 37° C. shaker bath for 40 minutes, with the buffer containing 0.1% collagenase and 0.1% BSA, and bubbled with 95% $O_2$ and 5% $CO_2$. The tissues are passed twice through a 5 ml glass syringe to liberate the gastric glands, and then filtered through 200 mesh nylon. The filtered glands are centrifuged at 270 g for 5 minutes and washed twice by resuspension and centrifugation.

The washed guinea pig gastric glands are resuspended in 25 ml of standard buffer containing 0.25 mg/ml of bacitracin. For binding studies, 10 μl of buffer (for total binding) or gastrin (1 μM final concentration, for nonspecific binding) or test compound and 10 μl of $^{125}$I-gastrin (NEN, 2200 Ci/mmole, 25 pM final) or $^3$H-pentagastrin (NEN 22 Ci/mmole, 1 nM final) are added to 220 μl of gastric glands in triplicate tubes which are aerated with 95% $O_2$ and 5% $CO_2$ and capped. The reaction mixtures, after incubation at 25° C. for 30 minutes, are filtered under reduced pressure on glass G/F B filters (Whatman) and immediately washed with 4×4 ml of standard buffer containing 0.1% BSA. The radioactivity on the filters is measured using a Beckman gamma 5500 for $^{125}$I-gastrin or liquid scintillation counting for $^3$H-pentagastrin.

The ability of the instant 3-substituted 1,4-benzodiazepines with 5- and 6-membered heterocylic rings to antagonize CCK and gastrin makes these compounds useful as pharmaceutical agents for mammals, especially for humans, for the treatment and prevention of disorders wherein CCK and/or gastrin may be involved. Examples of such disease states include gastrointestinal disorders, especially such as irritable bowel syndrome or ulcers, excess pancreatic or gastric secretion, acute pancreatitis, motility disorders or gastrointestinal neoplasms; central nervous system disorders, caused by CCK interactions with dopamine, such as neuroleptic disorders, tardive dyskinesia, Parkinson's disease, psychosis or Gilles de la Tourette Syndrome; disorders of appetite regulatory systems; Zollinger-Ellison syndrome, antral G cell hyperplasia, or pain (by the potentiation and prolongation of opiate-mediated analgesia); as well as certain tumors of the lower esophagus, stomach, intestines and colon.

The compounds of the instant invention or pharmaceutically-acceptable salts thereof, may be administered to a human subject either alone or, preferably, in combination with pharmaceutically-acceptable carriers or diluents, optionally with known adjuvants, such as alum, in a pharmaceutical composition, according to standard pharmaceutical practice. The compounds can be administered orally or parenterally, including intravenous, intramuscular, intraperitoneal, subcutaneous and topical administration.

For oral use of an antagonist of CCK, according to this invention, the selected compounds may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

When a compound according to the instant invention, or a salt thereof, is used as an antagonist or CCK or gastrin in a human subject, the daily dosage will normally be determined by the prescribing physician with the dosage generally varying according to the age, weight, and response of the individual patient, as well as the severity of the patient's symptoms. However, in most instances, an effective daily dosage will be in the range of from about 0.05 mg/kg to about 50 mg/kg of body weight, and preferably, of from 0.5 mg/kg to about 20 mg/kg of body weight, administered in single or divided doses. In some cases, however, it may be necessary to use dosages outside these limits.

In the treatment of irritable bowel syndrome, for instance, 1 to 10 mg/kg of a CCK antagonist might be administered orally (p.o.), divided into two doses per day (b.i.d.). In treating delayed gastric emptying, the dosage range would probably be the same, although the drug might be administered either intravenously (I.V.) or orally, with the I.V. dose probably tending to be slightly lower due to better availability. Acute pancreatitis might be treated preferentially in an I.V. form, whereas spasm and/or reflex esophageal, chronic pancreatitis, past vagatomy diarrhea, or treatment of anorexia or of pain associated with biliary dyskinesia might indicate p.o. form administration.

In the use of a gastrin antagonist as a tumor palliative for gastrointestinal neoplasms with gastrin receptors, as a modulator of central nervous system activity, treatment of Zollinger-Ellison syndrome, or in the treatment of peptic ulcer disease, a dosage of 0.1 to 10 mg/kg administered one-to-four times daily might be indicated.

Because these compounds antagonize the function of CCK in animals, they may also be used as feed additives to increase the food intake of animals, in amounts of from about 0.05 mg/kg to about 50 mg/kg of body weight.

The invention is further defined by reference to the following examples which are intended to be illustrative and not limiting.

EXAMPLE 1

Preparation of 2,4-dihydro-6-phenyl-1H-imidazo[1,2-a][1,4]benzodiazepine (16, $X^1$=H, $R^2$=Ph, Y is absent)

This compound is prepared according to the method of Earley, et al, *J. Med. Chem.*, 11, 774–777 (1968).

EXAMPLE 2

Preparation of 2,4-dihydro-4-oximino-6-phenyl-1H-imidazo[1,2-a]-1,4-benzodiazepine (58, $X^1$=H, $R^2$=Ph, Y is absent, Z=N)

To a suspension of potassium tert-butoxide (24.9 g, 222 mmole) in 600 mL of dry tetrahydrofuran is added 200 mL of dry tert-butylalcohol at −20° C. under nitrogen. 2,4-Dihydro-6-phenyl-1H-imidazo[1,2-a]-[1,4]-benzodiazepine (25 g) in 260 mL of tetrahydrofuran is added to this solution via addition funnel with the resulting solution being stirred for about 2 hours at −20° C. and treated with 17.4 mL (130 mmole) of isoamyl nitrite. The reaction mixture is warmed to 0° C. over approximately 15 minutes and quenched with the addition of 60 mL of cold water and 20 mL of glacial acetic acid and all solvents are removed under reduced pressure. The residue is partitioned between ethyl acetate (600 mL) and brine (100 mL), with the phases being separated and the organic extracts dried ($Na_2SO_4$) and concentrated. The resulting product is triturated with ether to give Compound (58).

EXAMPLE 3

Preparation of 4(R,S)-amino-2,4-dihydro-6-phenyl-1H-imidazo[1,2-a]-1,4-benzodiazepine (26, $X^1$=H, $R^2$=Ph, Y is absent, Z=N, n=Zero)

A solution of 150 mL of methanol containing 5 g 2,4-dihydro-4-oximino-6-phenyl-1H-imidazo[1,2-a]-[1,4]-benzodiazepine is treated with a slurry of active Raney-nickel catalyst[1] in ethanol (10 g). The resulting suspension is hydrogenated on a Parr apparatus at 60 psi and 23° C. for about 30 hours, and the catalyst is removed by filtration. The filtrate is concentrated to afford the title compound.

[1]The Raney-Nickel catalyst is prepared according to Fieser & Fieser, *Reagents for Organic Synthesis*, Vol. I, John Wiley & Sons, Inc., New York 1967, p. 729.

EXAMPLE 4

Preparation of 4(R,S)-(2(S)-tert-butoxycarbonylamino-3-phenyl-propanoylamino)-2,4-dihydro-6-phenyl-1H-imidazo[1,2-a]-[1,4]-benzodiazepine Crude 4(R,S)-amino-2,4-dihydro-6-phenyl-1H-imidazo-[1,2-a]-[1,4]-benzodiazepine (1.37 g), Boc-L-phenyl-alanine (1.37 g, 5.17 mmole), 1-hydroxybenzotriazole (0.07 g, 5.17 mmole), and 1-ethyl-3-(3-dimethylaminopropyl)carbodimide hydrochloride (0.99 g, 5.17 mmole) are combined in DMF (30 mL) and stirred at room temperature. The pH of the reaction mixture is adjusted to 8.5 with triethylamine, and after ½ hour, the DMF is removed in vacuo, and the residue partitioned between ethyl acetate and 10% citric acid solution (10 mL). The layers are separated and the organic phase is washed with sodium bicarbonate solution ($NaHCO_3$, saturated). The combined organic layers are washed with brine, dried over $Na_2SO_4$, filtered, and evaporated to dryness in vacuo to give the title compound as a mixture of diastereomers.

EXAMPLE 5

Preparation of 4(R and S)-(2(S)-amino-3-phenylpropanoylamino)-2,4-dihydro-6-phenyl-1H-imidazo[1,2-a]-[1,4]-benzodiazepine 4(RS)-(2(S)-tert-Butoxycarbonylamino-3-phenyl-propanoylamino)-2,4-dihydro-6-phenyl-1H-imidazo[1,2-a]-[2,4]-benzodiazepine (1.8 gm) is dissolved in EtOAc (25 mL), cooled to 0° C., and the solution saturated with HCl (g) over a 10 minute period. After stirring an additional 10 minutes, the solvent is removed in vacuo. The residue is dissolved in $H_2O$, basified with saturated $Na_2CO_3$ (aqueous) and extracted with EtOAc (3x). The organic layers are combined, washed wih brine, dried over $Na_2SO_4$, filtered and rotoevaporated in vacuo, with flash chromatography on silica gel separating the 1/1 pair of diastereomers into an upper and a lower component. The individual fractions containing the components are concentrated to dryness to give the separated diastereomers.

EXAMPLE 6

4(R)- and 4(S)-Amino-2,4-dihydro-6-phenyl-1H-imidazo[1,2-a]-[1,4]-benzodiazepine 4(S)-(2(S)-Amino-3-phenylpropanoylamino)-2,4-dihydro-6-phenyl-1H-imidazo[1,2-a][1,4]-benzodiazepine (1.15 g) is combined with phenylisothiocyanate (395 mg, 2.93 mmole) in $CH_2Cl_2$ (20 mL) and the mixture is concentrated on a steam bath. The resulting product is twice diluted with $CH_2Cl_2$ (20 mL), both times being reconcentrated on the steam bath. The product is evaporated in vacuo and treated with TFA (15 mL) and warmed for 18 minutes in an oil bath thermostated at 52°. The TFA is removed in vacuo, and the residue is treated twice with $CH_2Cl_2$ and with $Et_2O$ (being evaporated in vacuo after each treatment) and the resulting product is chromatographed on silica gel. The product fractions are evaporated in vacuo, and the residue is dissolved in $CH_2Cl_2$, washed with a small volume of 5% NaOH, dried over $Na_2SO_4$, filtered, and evaporated to give the 4-(S) isomer of the title structure.

4(R)-(2(S)-amino-3-phenylpropanoylamino)-6-2,4-dihydro-phenyl-1H-imidazo[1,2-a]-[1,4]-benzodiazepine is converted by the same procedure to the 4-(R) enantiomer of the title compound.

EXAMPLE 7

4(S)-2,4-Dihydro-4-(2-indolecarbonylamino)-6-phenyl-1H-imidazo-[1,2-a]-[1,4]-benzodiazepine (30, $X^1$=H, $R^2$=Ph, $R^3$=NHCO-2-indole, Y is absent, Z=N)

4(S)-4-Amino-6-phenyl-1H-imidazo[1,2-a]-[1,4]-benzodiazepine (595 mg) is dissolved in $CH_2Cl_2$ (15 mL) and treated with 2-indolecarbonyl chloride (403 mg, 2.24 mmole), followed by triethylamine (227 mg, 2.24 mmole). The mixture is stirred at room temperature for approximately 30 minutes and concentrated in vacuo. The residue is chromatographed on silica gel and the combined product fractions are evaporated to dryness in vacuo, before $Et_2O$ (15 mL) is added three times and evaporated in vacuo to give the title compound.

EXAMPLE 8

4(R)-2,4-Dihydro-4(3-Methoxyphenylaminocarbonylamino)-6-phenyl-1H-imidazo[1,2-a]-[1,4]-benzodiazepine (29, $X^1$=H, $R^2$=Ph,

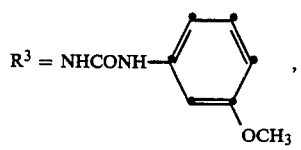

Y is absent, Z=N

To a solution of 85 mg of 4(R)-amino-2,4 dihydro-6-1H-imidazo-[1,2-a]-1,4-benzodiazepine in 8 ml of dry tetrahydrofuran is added 3-methoxyphenylisocyanate (40 μl, 0.315 mmole) at room temperature. Stirring is continued for 8 more hours and the reaction mixture is filtered with the collected product being washed with hot methanol and dried in vacuo.

EXAMPLE 9

7-Phenyl-1,2,3,5-tetrahydropyrido[1,2-a][1,4]benzodiazepine (16, $X^1$=H, $R^2$=phenyl, Y=$CH_2$)

This compound is prepared according to the method of Example 1 using carbobenzoxypropylamine to furnish a fused 6-membered heterocycle rather than a 5-membered one.

EXAMPLE 10

5-Oximino-7-phenyl-1,2,3,5-tetrahydropyrido[1,2-a]-[1,4]-benzodiazepine(25, $X^1$=H, $R^2$=Ph, Y=$CH_2$, Z=N)

This compound is prepared according to the method of Example 2.

EXAMPLE 11

5-Amino-7-phenyl-1,2,3,5-tetrahydropyrido[1,2-a]-[1,4]-benzodiazepine (26, $X^1$=H, $R^2$=Ph, Y=$CH_2$, Z=N, n=0)

This compound is prepared according to the method of Example 3 and resolved according to the methods of Examples 4 through 6.

EXAMPLE 12

5(S)-5-(2-Indolecarbonylamino)-7-phenyl-1,2,3,5-tetrahydropyrido-[1,2-a]-[1,4]-benzodiazepine (30, $X^1$=H, $R^2$=phenyl, $R^3$=NHCO-2-indole, Y=$CH_2$, Z=N)

This compound is prepared according to the method of Example 7.

EXAMPLE 13

5(R)-5-(3-Methylphenylaminocarbonylamino)-7-phenyl-1,2,3,5-tetrahydropyrido[1,2-a]-[1,4]-benzodiazepine (29, $X^1$=H, $R^2$=phenyl,

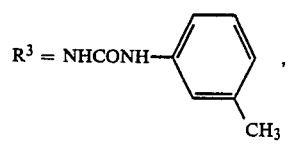

Y=$CH_2$, Z=N)

This compound is prepared according to the method of Example 8.

EXAMPLE 14

6-Phenyl-2,3,3a,4-tetrahydro-1H-pyrrolo[1,2-a]-[1,4]-benzodiazepine (6, $X^1$=H, Y is absent)

This compound is prepared according to the methods of Müller and Strauss, Helv. Chim, Acta, 65, 2118–2132 (1982).

EXAMPLE 15

4-Oximino-6-phenyl-2,3,3a,4-tetrahydro-1H-pyrrolo-[1,2a]-[1,4]-benzodiazepine (25, $X^1$=H, $R^2$=Ph, Y is absent, Z=$CH_2$)

This compound is prepared according to the method of Example 2 using lityium diisopropylamide in place of potassium tert-butoxide.

EXAMPLE 16

4-Amino-6-phenyl-2,3,3a,4-tetrahydro-1H-pyrrolo-[1,2-a]-[1,4]-benzodiazepine (26, $X^1$=H, $R^2$=Ph, Y is absent, Z=$CH_2$, n=0)

This compound is prepared according to the method of Example 3, with the 2 diastereomers being separated chromatographically and resolved according to the methods of Examples 4 through 6.

EXAMPLE 17

4(S)-4-(2-Indolecarbonylamino)-6-phenyl-2,3,3a,4-tetrahydro-1H-pyrrolo[1,2-a]-[1,4]-benzodiazepine (30, $X^1$=H, $R^2$=Ph, $R^3$=NHCO-2-indole, Y is absent, Z=$CH_2$)

This compound (either configuration at position 3a) is prepared according to the method of Example 7.

EXAMPLE 18

4(R)-4-(3-Methoxyphenylaminocarbonylamino)-6-phenyl-2,3,3a,4-tetrahydro-1H-pyrrolo[1,2-a]-[1,4]-benzodiazepine (29, $X^1$=H, Y is absent, Z=$CH_2$, $R^2$=Ph, $R^3$ = NHCONH— 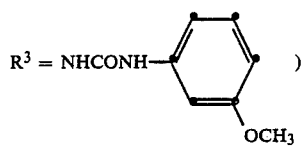 )

This compound (either configuration at position 3a) is prepared according to the method of Example 8.

EXAMPLE 19

7-Phenyl-1,2,3,4,4a,5-hexahydropyrido[1,2-a]-[1,4]benzodiazepine (6, $X^1$=H, Y=$CH_2$)

This compound is prepared according to the methods of Müller and Strauss, *Helv. Chim. Acta*, 65, 2118–2132 (1982).

EXAMPLE 20

5-Oximino-7-phenyl-1,2,3,4,4a,5-hexahydropyrido-[1,2-a][1,4]benzodiazepine(25, $X^1$=H, $R^2$=Ph, Y=$CH_2$, Z=$CH_2$)

This compound is prepared according to the method of Example 15.

EXAMPLE 21

5-Amino-7-phenyl-1,2,3,4,4a,5-hexahydropyrido-[1,2-a][1,4]benzodiazepine (26, $X^1$=H, $R^2$=Ph, Y=$CH_2$, Z=$CH_2$, n=0)

This compound is prepared according to the method of Example 3, with the diastereomers being separated chromatographically and resolved according to the methods of Examples 4 through 6.

EXAMPLE 22

5(R)-5-(3-Methylphenylaminocarbonylamino)-7-phenyl-1,2,3,4,4a,5-hexahydropyrido-[1,2-a][1,4]benzodiazepine (29, $X^1$=H, $R^2$=Ph, $R^3$ = NHCONH— 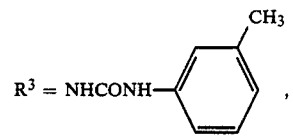 ,

Y=$CH_2$, Z=$CH_2$)

This compound (either configuration at position 4a) is prepared according to the method of Example 8.

EXAMPLE 23

5-(S)-5-(4-Chlorophenylcarbonylamino)-7-phenyl-1,2,3,4,4a,5-hexahydropyrido[1,2-a][1,4]benzodiazepine (30, $X^1$=H, $R^2$=Ph, $R^3$ = NHCO— 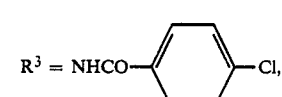 —Cl,

Y=Z=$CH_2$)

This compound (either configuration at position 4a) is prepared according to the method of Example 7.

EXAMPLE 24

3-Methyl-7-phenyl-1,2,3,4,4a,5-hexahydropyrazino-[1,2-a][1,4]-benzodiazepine (12, $X^1$=H, $R^2$=Ph or 6, $X^1$=H, Y=N—$CH_3$)

This compound is prepared according to the methods of Müller and Strauss, *Helv. Chim. Acta*, 65, 2118–2132 (1982), or Smith et al., *J. Med. Chem*, 23, 952–955 (1980).

EXAMPLE 25

3-Methyl-5-oximino-7-phenyl-1,2,3,4,4a,5-hexahydropyrazino-benzodiazepine (25, $X^1$=H, $R^2$=Ph, Y=N—$CH_3$ Z=$CH_2$)

This compound is prepared according to the method of Example 15.

EXAMPLE 26

5-Amino-3-methyl-7-phenyl-1,2,3,4,4a,5-hexahydropyrazino[1,2-a][1,4]benzodiazepine (26, $X^1$=H, $R^2$=Ph, Y=N—$CH_3$, Z=$CH_2$, n=0)

This compound is prepared according to the method of Example 3 (either configuration at position 4a) and resolved according to the methods of Examples 4 through 6.

EXAMPLE 27

5(S)-5-(2-Indolecarbonylamino)-3-methyl-7-phenyl-1,2,3,4,4a,5-hexahydropyrazino[1,2-a][1,4]-benzodiazepine (30, $X^1$=H, $R^2$=Ph, $R^3$NHCO-2-indole, Y=N—$CH_3$, Z=$CH_2$)

This compound (either configuration at position 4a) is prepared according to the method of Example 7.

EXAMPLE 28

5(R)-5-(3-Chlorophenylaminocarbonylamino)-3-methyl-7-phenyl-1,2,3,4,4a,5-hexahydropyrazino[1,2-a][1,4]-benzodiazepine (29, $X^1$=H, $R^2$=Ph, $R^3$ = NHCONH— 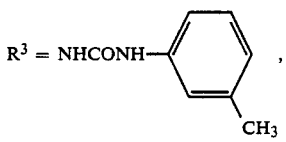 , $CH_3$

Y=N—$CH_3$, Z=$CH_2$)

This compound (either configuration at position 4a) is prepared according to the method of Example 8.

What is claimed is:

1. A compound of the formula:

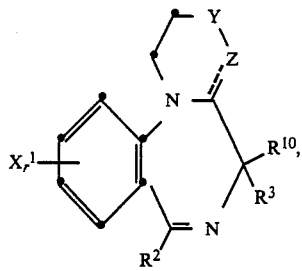 (I)

wherein
R¹ is H, or $C_1$-$C_4$-straight- or branched-chain alkyl;
R² is H, $C_1$-$C_4$-straight- or branched-chain alkyl, mono- or disubstituted or unsubstituted phenyl, where the substituent(s) is/are independently selected from the group consisting of halo, $C_1$-$C_4$-alkyl, $C_1$-$C_4$-alkoxy, $C_1$-$C_4$-alkylthio, carboxyl, carboxyl-$C_1$-$C_4$-alkyl, nitro, —$CF_3$,

and hydroxy, 2-, 3-, or 4-pyridyl, or —$(CH_2)_m COOR^6$;
R³ is

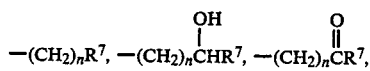

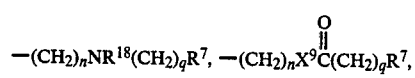

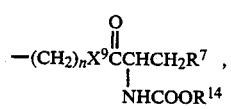

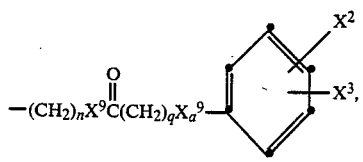

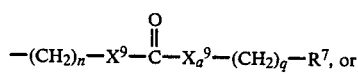

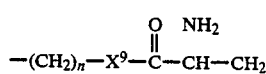

R⁴ and R⁵ are independently H, $C_1$-$C_4$-straight- or branched-chain-alkyl, cyclo-$C_3$-$C_7$-alkyl, or are connected to nitrogen to form a hetero ring of the form

where k is 2 to 6;
R⁶ is H, $C_1$-$C_4$-straight or branched-chain alkyl, cyclo-$C_3$-$C_7$-alkyl, unsubstituted or mono- or disubstituted phenyl, where the substituent(s) is/are independently selected from the group consisting of halo, $C_1$-$C_4$-alkyl, $C_1$-$C_4$-alkoxy, nitro, and $CF_3$, or unsubstituted or mono- or disubstituted phenyl-$C_1$-$C_4$-straight or branched-chain alkyl, where the substituent(s) is/are independently selected from the group consisting of halo, $C_1$-$C_4$-alkyl, $C_1$-$C_4$-alkoxy, nitro, and $CF_3$;

R⁷ is α- or β-naphthyl, unsubstituted or mono- or disubstituted phenyl, where the substituent(s) is/are independently selected from the group consisting of halo, —$NO_2$, —OH, —$NR^4R^5$,

as defined above, $C_1$-$C_4$-straight- or branched-chain alkyl, cyano, phenyl, trifluoromethyl, acetylamino, acetyloxy, $C_1$-$C_4$-straight- or branched-chain alkylthio, $SCF_3$, C≡CH, $CH_2SCF_3$, $OCHF_2$, S-phenyl, and $C_1$-$C_4$-straight- or branched-chain alkoxy,

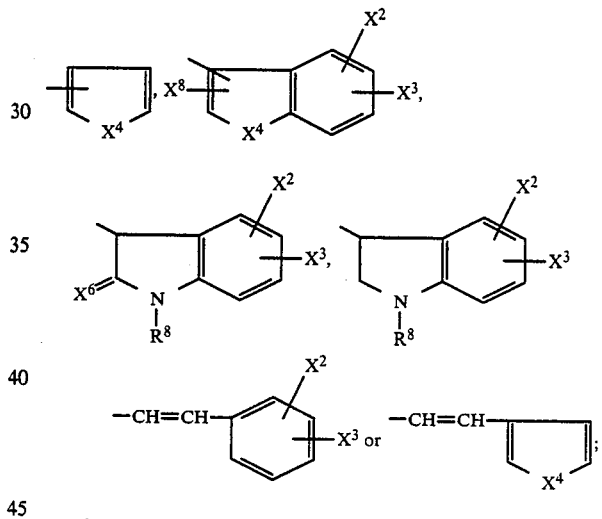

R⁸ is H, $C_1$-$C_4$-straight- or branched-chain alkyl, cyclo-$C_3$-$C_7$-alkyl, —$(CH_2)_n$-cyclo-$C_3$-$C_7$-alkyl,

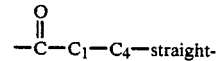

or branched-chain alkyl, or

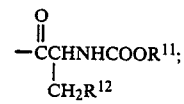

R¹⁰ is H, —OH, or —$CH_3$;
R¹¹ and R¹² are independently $C_1$-$C_4$-straight- or branched-chain alkyl or cyclo-$C_3$-$C_7$-alkyl;
R¹⁴ is $C_1$-$C_4$-straight- or branched-chain alkyl or phenyl-$C_1$-$C_4$-straight- or branched-chain alkyl;
R¹⁸ is H, $C_1$-$C_4$-straight- or branched-chain alkyl or formyl, acetyl, propionyl or butyryl;
m is 1-to-4;
n is 0-to-4;

q is 0-to-4;
r is 1 or 2;
$X^1$ is H, $-NO_2$, $CF_3$, CN, OH, $C_1$–$C_4$-straight- or branched-chain alkyl, halo, $C_1$–$C_4$-straight- or branched-chain alkylthio, $C_1$–$C_4$-straight- or branched-chain alkoxy, $-(CH_2)_nCOOR^6$, $-NR^4R^5$, or $$O-\overset{\overset{O}{\|}}{C}-R^4;$$

$X^2$ and $X^3$ are independently H, $-OH$, $-NO_2$, halo, $C_1$–$C_4$-straight- or branched-chain alkylthio, $C_1$–$C_4$-straight- or branched-chain alkyl, $C_1$–$C_4$-straight- or branched-chain alkoxy, or $$O-\overset{\overset{O}{\|}}{C}-R^4;$$

$X^4$ is S, O, $CH_2$, or $NR^8$;
$X^6$ is O;
$X_8$ is H or $C_1$–$C_4$-straight- or branched-chain alkyl;
$X^9$ and $X_a{}^9$ are independently $NR^{18}$ or O;
$Y = CH_2$ or $NR^1$; and
$Z = N$ or $CH_2$,
or a pharmaceutically-acceptable salt thereof.

2. A compound according to claim 1, wherein $R^1$ is H or $C_1$–$C_4$-alkyl;
$R^2$ is unsubstituted of mono- or disubstituted phenyl, where the substituent(s) is/are independently selected from the group consisting of halo, $C_1$–$C_4$-alkyl, $C_1$–$C_4$-alkoxy, nitro, and $-CF_3$;
$R^3$ is $-(CH_2)_nR^7$, $$-(CH_2)_nX^9\overset{\overset{O}{\|}}{C}(CH_2)_qR^7$$

or $$-(CH_2)_n-X^9-\overset{\overset{O}{\|}}{C}-X_a{}^a-(CH_2)_n-R^7;$$

$R^7$ is $\alpha$- or $\beta$-naphthyl, unsubstituted or mono- or disubstituted phenyl, where the substituent(s) is/are independently selected from the group consisting of halo, nitro, $C_1$–$C_4$-alkyl, trifluoromethyl and $C_1$–$C_4$-alkoxy,

[structures with $X^2$, $X^3$, $X^4$, $X^8$, or $-CH=CH-$ phenyl with $X^2$, $X^3$]

$R^8$ is H, or $C_1$–$C_4$-alkyl;
n is 0-to-2;
q is 0-to-2;
r is 1 or 2;
$X^1$ is H, $-NO_2$, $C_1$–$C_4$-alkyl, halo, or $C_1$–$C_4$-alkoxy;
$X^2$ and $X^3$ are independently H, $-NO_2$, halo, $C_1$–$C_4$-alkyl or $C_1$–$C_4$-alkoxy;
$X^4$ is S, O, $CH_2$, or $NR^8$;
$X^8$ is H or $C_1$–$C_4$-alkyl;

$X^9$ and $X_a{}^9$ are independently NH or O;
or a pharmaceutically-acceptable salt thereof.

3. A compound according to claim 1, wherein
$R^1$ is H or methyl;
$R^2$ is phenyl or o-F-phenyl;
$R^3$ is $$\overset{\overset{O}{\|}}{NHC}-R^7 \text{ or } \overset{\overset{O}{\|}}{NHCNH}-R^7;$$

$R^7$ is

[indole structure], [phenyl with $X^2$],

[phenyl with $X^2$] or [phenyl with $X^2$];

$X^1$ is H;
$X^2$ is H, $-NO_2$, halo, methyl, or methoxy.

4. A compound according to claim 1, wherein
$R^2$ is phenyl or o-F-phenyl;
$R^3$ is $$\overset{\overset{O}{\|}}{NHC}-R^7 \text{ or } \overset{\overset{O}{\|}}{NHCNH}-R^7;$$

$R^7$ is

[indole structure], [phenyl with $X^2$],

[phenyl with $X^2$] or [phenyl with $X^2$];

$X^1$ is H;
$X^2$ is H, $-NO_2$, halo, methyl, or methoxy;
Y is $CH_2$; and
Z is $CH_2$.

5. A compound according to claim 1, wherein
$R^2$ is phenyl or o-F-phenyl; $R^3$ is $$\overset{\overset{O}{\|}}{NHC}-R^7 \text{ or } \overset{\overset{O}{\|}}{NHCNH}-R^7;$$

$R^7$ is

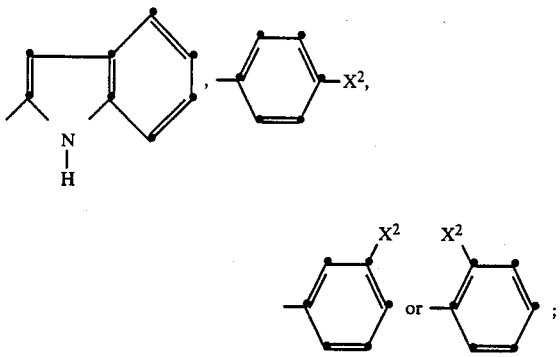

$X^1$ is H;
$X^2$ is H, $-NO_2$, halo, methyl, or methoxy;
Y is N-CH$_3$; and
Z is N.

6. A compound according to claim 1, wherein
$R^2$ is phenyl or o-F-phenyl;
$R^3$ is

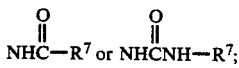

$R^7$ is

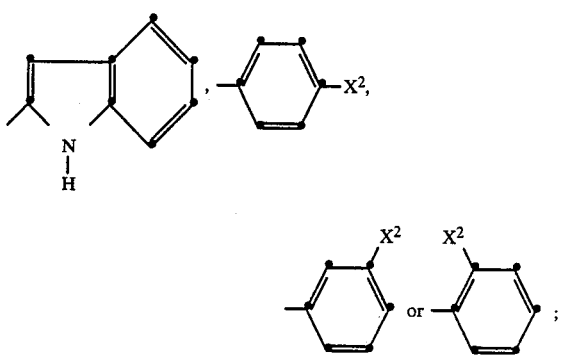

$X^1$ is H;
$X^2$ is H, $-NO_2$, halo, methyl, or methoxy;
Y is CH$_2$; and
Z is N.

7. A compound according to claim 1 which is:

5(S)-5(4-chlorophenylcarbonylamino)-7-phenyl-1,2,3,4,4a,5-hexahydropyrido-[1,2-a]-[1,4]-benzodiazepine;

5(S)-5-(2-indolecarbonylamino)-3-methyl-7-phenyl-1,2,3,4,4a,5-hexahydro-pyrazino[1,2a]-[1,4]-benzodiazepine; or 5(S)-5-(2-indolecarbonylamino)-7-phenyl-1,2,3,5-tetrahydropyrido[1,2-a]-[1,4]-benzodiazepine.

8. A compound according to claim 1 which is:

5(R)-5-(3-methylphenylaminocarbonylamino)-7-phenyl-1,2,3,4,4a,5-hexahydropyrido-[1,2,-a]-[1,4]-benzodiazepine;

5(R)-5-(3-chlorophenylaminocarbonylamino)-3-methyl-7-phenyl-1,2,3,4,4a,5-hexahydroprazino-[1,2-a]-[1,4]-benzodiazepine; or 5(R)-5-(3-methylphenylaminocarbonylamino)-7-phenyl-1,2,3,5-tetrahydropyrido-[1,2-a]-[1,4]-benzodiazepine.

9. A pharmaceutical composition comprising a therapeutically-effective amount for antagonism of the function of cholecystokinins or gastrin in mammals of one or more compounds according to claim 1, or pharmaceutically-acceptable salts thereof, and a pharmaceutically-acceptable carrier.

10. A composition according to claim 9, further comprising an adjuvant.

11. A composition according to claim 9, wherein the therapeutically-effective amount is from about 0.05 to about 50 mg/kg of body weight.

12. A method of preventing in mammals or treating mammals for cholecystokinin or gastrin related disorders of the gastrointestinal, central nervous or appetite regulatory systems which comprises administering to those mammals a therapeutically-effective amount of one or more compounds or pharmaceutically-acceptable salts according to claim 1.

13. A method according to claim 12, wherein a pharmaceutically-acceptable carrier or a pharmaceutically-acceptable carrier and an adjuvant are also administered.

14. A method according to claim 13, wherein the mammals are humans and a therapeutically-effective amount is from about 0.1 to about 20 mg/kg of body weight, administered in single or divided doses.

15. A method of increasing food intake in animals which comprises administering approximately 0.05 mg/kg to 50 mg/kg of body weight of one or more compounds or pharmaceutically-acceptable salts according to claim 1.

* * * * *